United States Patent
Nuno et al.

(10) Patent No.: US 7,432,297 B2
(45) Date of Patent: Oct. 7, 2008

(54) REACTION PRODUCT OF RESORCIN AND METHYL ETHYL KETONE

(75) Inventors: Tatsumi Nuno, Toyonaka (JP); Tomokazu Nakamura, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 185 days.

(21) Appl. No.: 11/330,287

(22) Filed: Jan. 12, 2006

(65) Prior Publication Data

US 2006/0173153 A1    Aug. 3, 2006

(30) Foreign Application Priority Data

Jan. 18, 2005    (JP) .............................. 2005-009949

(51) Int. Cl.
*A61K 31/352* (2006.01)
*C07D 311/78* (2006.01)

(52) U.S. Cl. ..................................... 514/456; 549/406

(58) Field of Classification Search ................. 514/456; 549/406
See application file for complete search history.

(56) References Cited

U.S. PATENT DOCUMENTS 4,323,505 A * 4/1982 Hashimoto et al. .......... 549/408
5,698,717 A   12/1997 Iyama et al.

FOREIGN PATENT DOCUMENTS

EP       0 054 589 A    6/1982

EP       0 700 959 A    3/1996
JP       2003-277308 A  10/2003

OTHER PUBLICATIONS

Patent Abstracts of Japan, vol. 008, No. 003, Jan. 7, 1984 corresponds to JP 58-173176.

* cited by examiner

*Primary Examiner*—Taofiq A Solola
(74) *Attorney, Agent, or Firm*—Sughrue Mion, PLLC

(57) ABSTRACT

A compound of the following formula (I) or (II)

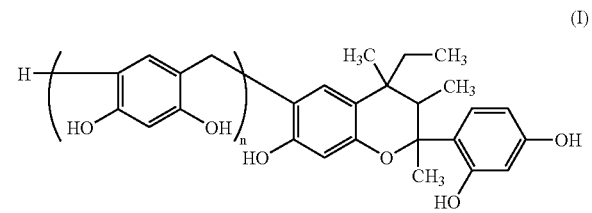

(in the formula (I), n represents an integer of 0 to 2)

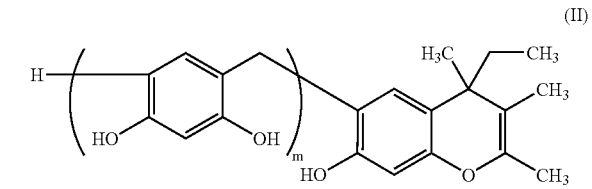

(in the formula (II), m represents an integer of 0 to 2).

8 Claims, 6 Drawing Sheets

REACTION PRODUCT OF RESORCIN AND METHYL ETHYL KETONE

TECHNICAL FIELD OF THE INVENTION

The present invention relates to a reaction product of resorcin and methyl ethyl ketone and a reaction product of resorcin, formaldehyde and methyl ethyl ketone.

RELATED ART OF THE INVENTION

A resorcin/formaldehyde resin is a resin obtained by a reaction of resorcin and formaldehyde and is used as an adhesive for various materials from the standpoints of a change of physical properties by heating, reactivity with other chemical materials, and the like (see, Japanese Patent Application Laid-Open (JP-A) No. 2003-277308).

However, the resorcin/formaldehyde resin described in the above-mentioned patent literature shows a poor physical property (rubber-like state) in reaction and manifests incorporation of non-reacted resorcin into the resin causing a large content of remaining resorcin in the resin, thereby leading to a problem of deterioration of working environments by transpiration of the remaining resorcin.

DISCLOSURE OF THE INVENTION

An object of the present invention is to provide a compound useful as an adhesive component.

Another object of the present invention is to provide an adhesive composition having low content of remaining resorcin.

The present inventors have intensively studied and resultantly found that a resin obtained by reacting resorcin, formaldehyde and methyl ethyl ketone in the presence of water, salts and acidic catalyst scarcely manifests the problem as described above and is suitable as an adhesive component.

That is, the present invention provides the following [1] to [9].

[1] A compound of the following formula (I).

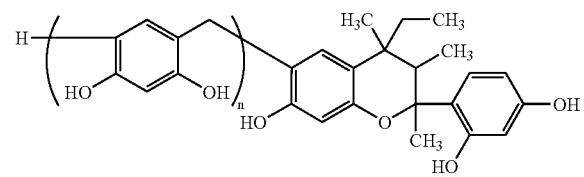

(in the formula (I), n represents an integer of 0 to 2)

[2] A compound of the following formula (II).

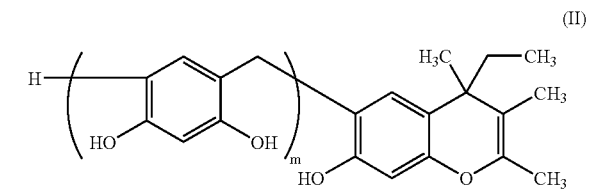

(in the formula (II), m represents an integer of 0 to 2)

[3] The compound according to [1], wherein the compound is a compound (1) of the following formula.

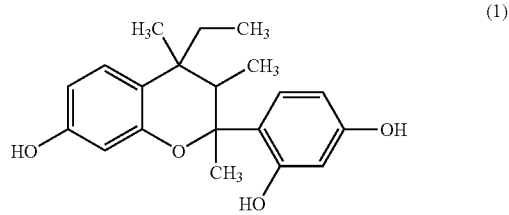

[4] The compound according to [2], wherein the compound is a compound (2) of the following formula.

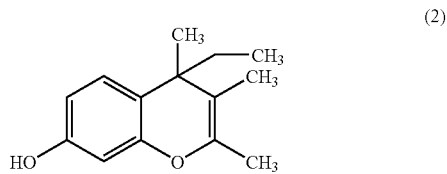

[5] The compound according to [1], wherein the compound is a compound (3) of the following formula.

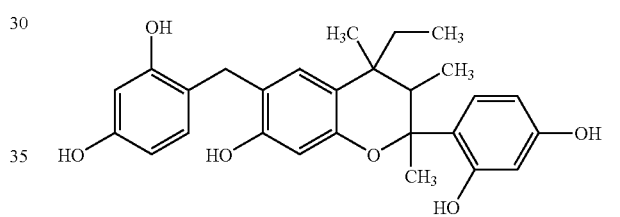

[6] The compound according to [1], wherein the compound is a compound (4) of the following formula.

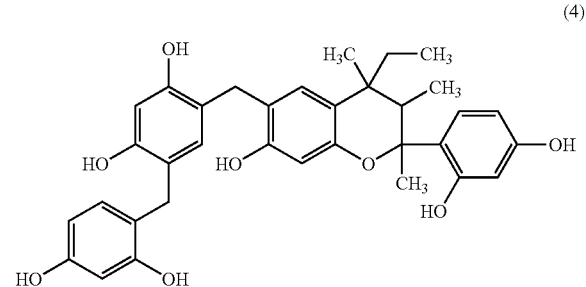

[7] The compound according to [2], wherein the compound is a compound (5) of the following formula.

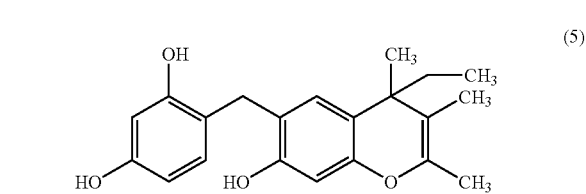

[8] The compound according to [2], wherein the compound is a compound (6) of the following formula.

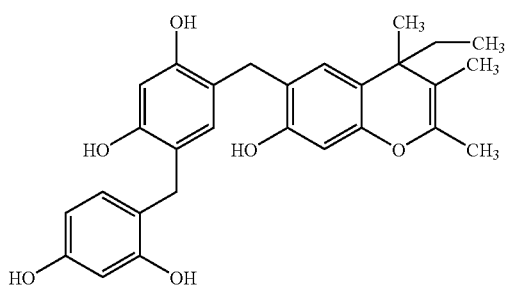
(6)

[9] An adhesive composition comprising at least one compound selected from the group consisting of compounds of the following formula (I)

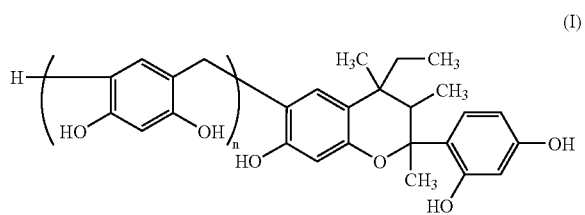
(I)

(in the formula (I), n represents an integer of 0 to 2) and at least one compound selected from the group consisting of compounds of the following formula (II)

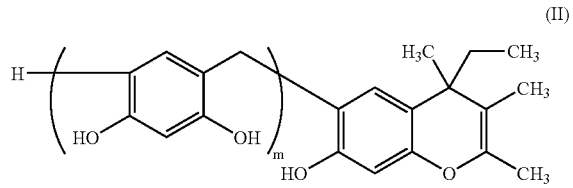
(II)

(in the formula (II), m represents an integer of 0 to 2).

[10] The adhesive composition according to [9], wherein the composition is obtained by reacting resorcin, formaldehyde and methyl ethyl ketone in the presence of water, salts and acidic catalyst.

[11] The adhesive composition according to [10], wherein the salts are calcium chloride, sodium sulfate or a mixture of calcium chloride and sodium sulfate.

[12] The adhesive composition according to [10] or [11], wherein the salts are used in an amount of 0.1 to 10 mol per mol of resorcin.

Here, compounds (1) and (2) correspond to reaction products of resorcin and methyl ethyl ketone, respectively. Further, compounds (3) and (4) correspond to reaction products of resorcin, formaldehyde and methyl ethyl ketone, respectively. Still further, compounds (5) and (6) correspond to other reaction products of resorcin, formaldehyde and methyl ethyl ketone, respectively.

MODES FOR CARRYING OUT THE INVENTION

Figure 1:
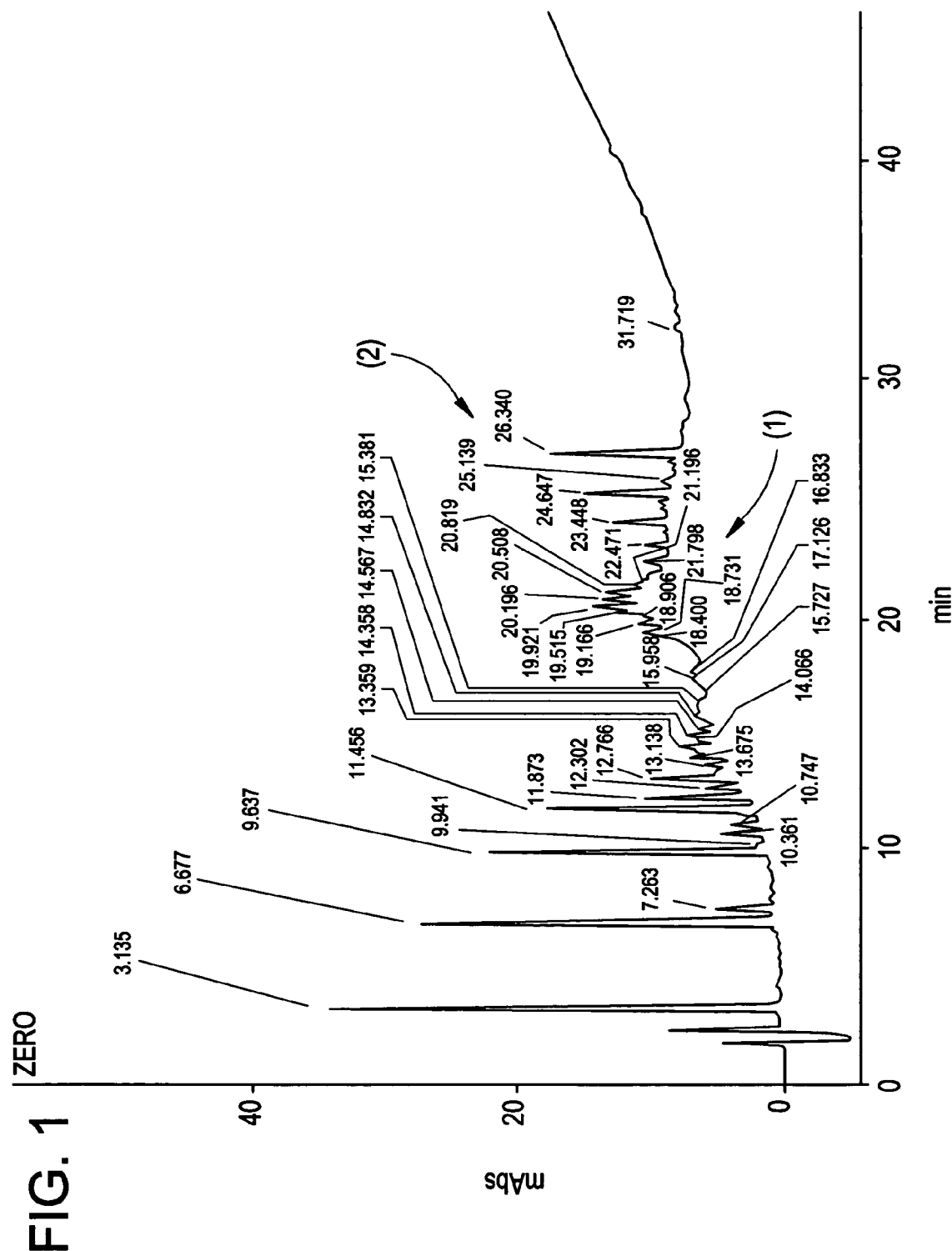
FIG. 1 is a view showing a liquid chromatography of a resorcin/formaldehyde/methyl ethyl ketone-based resin in the present invention.

The present invention will be described in detail below.

A compound of the formula (I) (hereinafter, abbreviated as compound (I) in some cases) and a compound of the formula (II) (hereinafter, abbreviated as compound (II) in some cases) described above and specific examples thereof (1) to (6) are obtained by separating, using a separating means such as liquid chromatography and the like, components in a resorcin/formaldehyde/methyl ethyl ketone resin produced by a production method including four processes described below.

(First Process)
A process of reacting resorcin, formaldehyde and methyl ethyl ketone in the presence of water, salts and acidic catalyst, under heating if necessary.

(Second Process)
A process of neutralizing the reaction liquid obtained in the first process, with an alkali.

(Third Process)
A process of separating the reaction liquid after neutralization obtained in the second process into an organic phase and an aqueous phase.

(Fourth Process)
A process of concentrating the organic phase after separation obtained in the third process.

The method of producing a resorcin/formaldehyde/methyl ethyl ketone resin will be illustrated below for each process.

The first process is a process of reacting resorcin, formaldehyde and methyl ethyl ketone, and the reaction is conducted in the presence of water, salts and acidic catalyst, if necessary while heating.

The formaldehyde used in the present invention includes a formaldehyde aqueous solution (e.g., formaldehyde concentration of formaldehyde aqueous solution is 37 wt %) and formaldehyde precursor. Examples of the formaldehyde precursor include cyclic formals such as p-formaldehyde, trioxane and the like and chain formals such as methylal and the like. As the formaldehyde, a formaldehyde aqueous solution is preferable.

In the above-mentioned reaction, the molar ratio of formaldehyde to resorcin is usually 0.3 to 1 mol per mol of resorcin, preferably 0.4 to 0.8 mol per mol of resorcin. Further, in the above-mentioned reaction, the molar ratio of methyl ethyl ketone to resorcin is usually 0.1 to 10 mol per mol of resorcin, preferably 0.5 to 5 mol per mol of resorcin.

Mentioned as the salts are sodium salts such as sodium citrate, sodium tartarate, sodium acetate, sodium chloride, sodium sulfate and the like, calcium salts such as calcium citrate, calcium tartarate, calcium chloride and the like, magnesium salts such as magnesium chloride, and the like of these salts, calcium chloride and sodium sulfate are particularly preferable.

The use amount of the salts is usually in the range of 0.01 to 100 mol, preferably of 0.1 to 30 mol, further preferably of 0.1 to 10 mol, further more preferably of 1 to 10 mol, per mol of resorcin.

The use amount of water in the above-mentioned method of producing a resorcin/formaldehyde/methyl ethyl ketone resin is usually in the range of 50 to 6000 parts by weight, preferably of 50 to 2000 parts by weight, more preferably 50 to 1000 parts by weight per 100 parts by weight of the total amount of resorcin, formaldehyde and methyl ethyl ketone. When an aqueous solution such as formalin is used as the formaldehyde, water contained in this aqueous solution is also included in the above-mentioned use amount.

The above-mentioned acidic catalyst includes inorganic acids such as hydrochloric acid, sulfuric acid, nitric acid, phosphoric acid and the like; heteropolyacids such as phosphotungstic acid, phosphomolybdic acid and the like; halogenated metal salts such as zinc chloride, aluminum chloride and the like; organic carboxylic acids such as trichloroacetic acid, acetic acid, oxalic acid and the like; organic sulfonic acids such as methanesulfonic acid, ethanesulfonic acid, p-toluenesulfonic acid, phenolsulfonic acid, and the like. These acidic catalysts are used singly or in admixture. As the acidic catalyst, hydrochloric acid, sulfuric acid and p-toluenesulfonic acid are preferable, and hydrochloric acid is particularly preferable.

The use amount of the acidic catalyst is usually in the range of 0.0000001 to 5 mol, preferably of 0.00001 to 2 mol, further preferably of 0.001 to 1 mol, per mol of resorcin.

The above-mentioned reaction temperature is usually in the range of 10 to 90° C., preferably of 20 to 80° C.

When an aqueous solution such as formalin is used as the formaldehyde in the above-mentioned reaction, the reaction may also be effected in a method in which methyl ethyl ketone is previously charged in a mixture of water, salts, resorcin and acidic catalyst if necessary under heating, then, formalin is dropped into the solution. Also, formalin and methyl ethyl ketone may be simultaneously added in parallel into a mixture of water, salts, resorcin and acidic catalyst and reacted if necessary under heating. Further, a part of formalin may be dropped into a mixture of water, salts, resorcin and acidic catalyst, then, the remaining formalin and all of methyl ethyl ketone may be simultaneously added in parallel and reacted if necessary under heating.

The reaction liquid obtained in the first process is neutralized with an alkali in the second process. It is preferable that the neutralization is conducted as quickly as possible. As the above-mentioned alkali, an ammonia gas or ammonia aqueous solution, sodium hydroxide or sodium hydroxide aqueous solution, potassium hydroxide or potassium hydroxide aqueous solution, sodium carbonate or sodium carbonate aqueous solution, potassium carbonate or potassium carbonate aqueous solution, calcium hydroxide or calcium hydroxide aqueous solution, and the like are used. When calcium chloride is used as the salts in the above-mentioned reaction, solid of calcium hydroxide or calcium hydroxide aqueous solution is preferable as the alkali.

The reaction liquid after neutralization obtained in the second process is separated into an organic phase and an aqueous phase in the third process.

In the organic phase, a resorcin/formaldehyde/methyl ethyl ketone resin containing non-reacted resorcin is present. In the aqueous phase, an aqueous solution containing salts is present.

The organic phase obtained in the third process is concentrated in the fourth process. Concentration in the fourth process is conducted for removing non-reacted methyl ethyl ketone remaining in the reaction liquid in the first process. Preferably, concentration is conducted by azeotropic distillation in the presence of water.

Azeotropic distillation may be conducted under atmospheric pressure or under reduced pressure. The amount of water in azeotropic distillation is usually about 0.5 to 10-fold by weight based on the organic phase described above.

After completion of concentration, the resulting resorcin/formaldehyde/methyl ethyl ketone resin may be diluted appropriately with water, alternatively, a base such as the above-mentioned alkali or the like may also be added for enhancing water-solubility of the above-mentioned resin. The preferable concentration of a resorcin/formaldehyde/methyl ethyl ketone resin is in the range of 20 to 60 wt %.

Regarding preferable molecular weight distribution in a resorcin/formaldehyde/methyl ethyl ketone resin of the present invention, those having a molecular weight of 164 to 1400 occupy about 40 wt % of the total amount. Regarding particularly preferable molecular weight distribution in a resorcin/formaldehyde/methyl ethyl ketone resin of the present invention, oligomer components satisfying the above-mentioned molecular weight distribution and having two partial structures derived from methyl ethyl ketone occupy about 10 wt % of the total amount.

It is preferable that the resulting resorcin/formaldehyde/methyl ethyl ketone resin contains at least one compound (I) and at least one compound (II). It is preferable that the resulting resorcin/formaldehyde/methyl ethyl ketone resin contains specific examples of compound (I) and compound (II), a compound (1), compound (2), compound (3), compound (4), compound (5) and compound (6).

The above-mentioned compounds (compounds (I), (II) and its specific examples, compounds (1)-(6)) may contain their isomers. The adhesive composition may also contain the isomers of the above-mentioned compounds.

The present invention can provide a compound (I) and a compound (II) useful as an adhesive component, and specific examples thereof, a compound (1), compound (2), compound (3), compound (4), compound (5) and compound (6).

Further, the present invention can provide a resorcin/formaldehyde/methyl ethyl ketone resin-based adhesive composition containing the above-mentioned compound (I) and compound (II) which is more excellent in adhesion as compared with conventional resorcin/formaldehyde resins, specifically, a resorcin/formaldehyde/methyl ethyl ketone resin-based adhesive composition containing compounds (1) to (6).

The resorcin/formaldehyde/methyl ethyl ketone resin of the present invention can be suitably used as an adhesive composition because of its low content of remaining resorcin and low viscosity.

EXAMPLES

The present invention will be illustrated further in detail based on examples below, but it is needless to say that the present invention is not limited to these examples.

Example 1

377.3 g of calcium chloride and 520.8 g of water were charged into a glass reaction vessel and stirred while cooling. To the resultant solution was added 121.1 g of resorcin and 31.2 g of 3.6% hydrochloric acid, and the solution was heated up to 54 to 74° C. and kept about 1 hour.

To the obtained solution, a mixture of 53.6 g of a 37% formalin aqueous solution and 66.9 g of water, and 110 g of methyl ethyl ketone were simultaneously dropped in parallel over about 1 hour while keeping the inner temperature at about 60° C. After completion of dropping, the solution was kept at the same temperature for about 1 hour.

After completion of thermal insulation, 1.5 g of calcium hydroxide was immediately charged and the solution was kept at about 60° C. for about 1 hour, then, stirring in the reaction vessel was stopped and the solution was allowed to stand still for about 10 minutes and separated to obtain an organic phase.

The organic phase obtained above was charged into a distillation apparatus, and 300.0 g of hot water of 60° C. was added, then, azeotropic distillation was conducted while stirring under conditions of bath temperature 100° C./100 to 80 kPa. During the azeotropic distillation, a distilling mixture of methyl ethyl ketone/water was removed out of the system while cooling with a cooling tube. The azeotropic distillation was completed when the amount of the remaining liquid in the vessel reached about 270 g and the solution was cooled down to about 50° C. after completion of azeotropic distillation.

30 g of 25% ammonia water was added to the remaining liquid in the vessel after distillation of a mixture of methyl ethyl ketone/water to give alkaline pH value. Then, the solution was stirred for about 1 hour at about 50° C. pH at this point was 8.5 About 300 g of a resorcin/formaldehyde/methyl ethyl ketone resin having a solid content of 50% was obtained. The resorcin content in this resin was 7.4%.

The above-mentioned resin was analyzed by liquid chromatography, to obtain the result shown in FIG. 1. The conditions for the liquid chromatography are shown below.

Apparatus: LC10AT type manufactured by Shimadzu Corp.

Column: Cadenza CD-C18 (4.6 mmΦ×150 mm, spherical diameter of filler: 3 μm, manufactured by Imtakt Co.)

Column thermostat temperature: 40° C.

Moving bed: solvent A (0.1% (v/v) trifluoroacetic acid aqueous solution), solvent B (0.1% (v/v) trifluoroacetic acid-containing acetonitrile)

Moving phase flow rate: 1 ml/min (wherein, solvent ratio A/B is 0.8 ml/0.2 ml at initiation, concentration gradient is provided so that the flow rate of solvent A is 1 ml after 40 minutes)

Sample injection amount: 10 μl

Sample concentration: 4 mg/ml (solvent: methanol)

Ultraviolet detector: wavelength 254 nm

Figure 2:
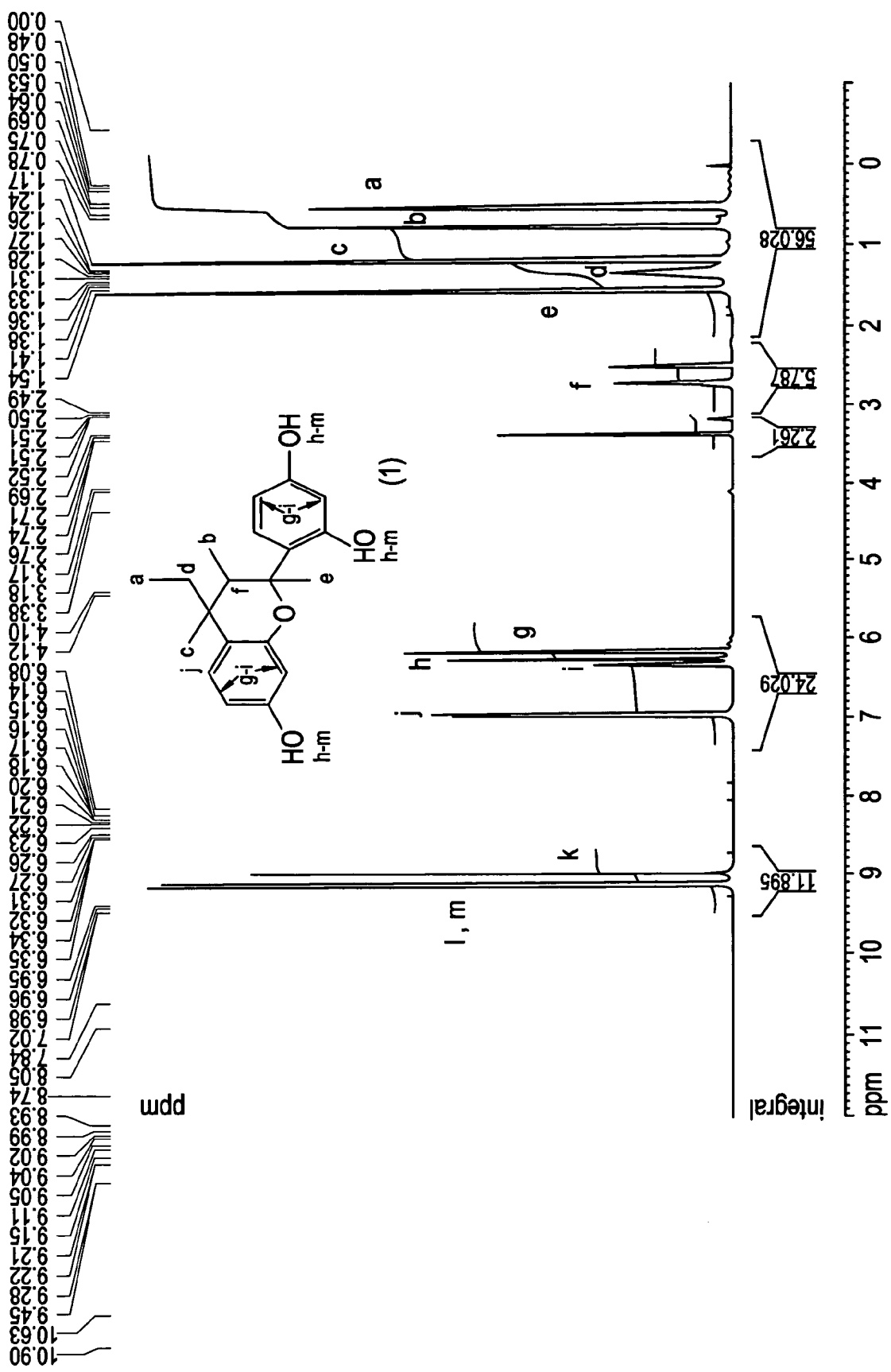
FIG. 2 is a view showing $^1$H-NMR of a compound (1) in the present invention.

Components at elution times of 21.8 minutes and 26.3 minutes in FIG. 1 were fractioned into columns. A component of an elution time of 21.8 minutes after fractioning was identified as a compound of the following formula (1) based on the result of its $^1$H-NMR (see FIG. 2, measuring solvent is heavy dimethyl sulfoxide).

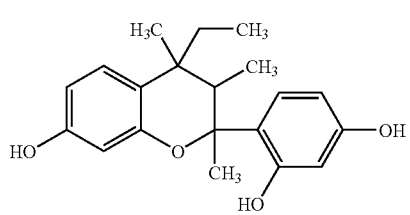
(1)

Figure 3:
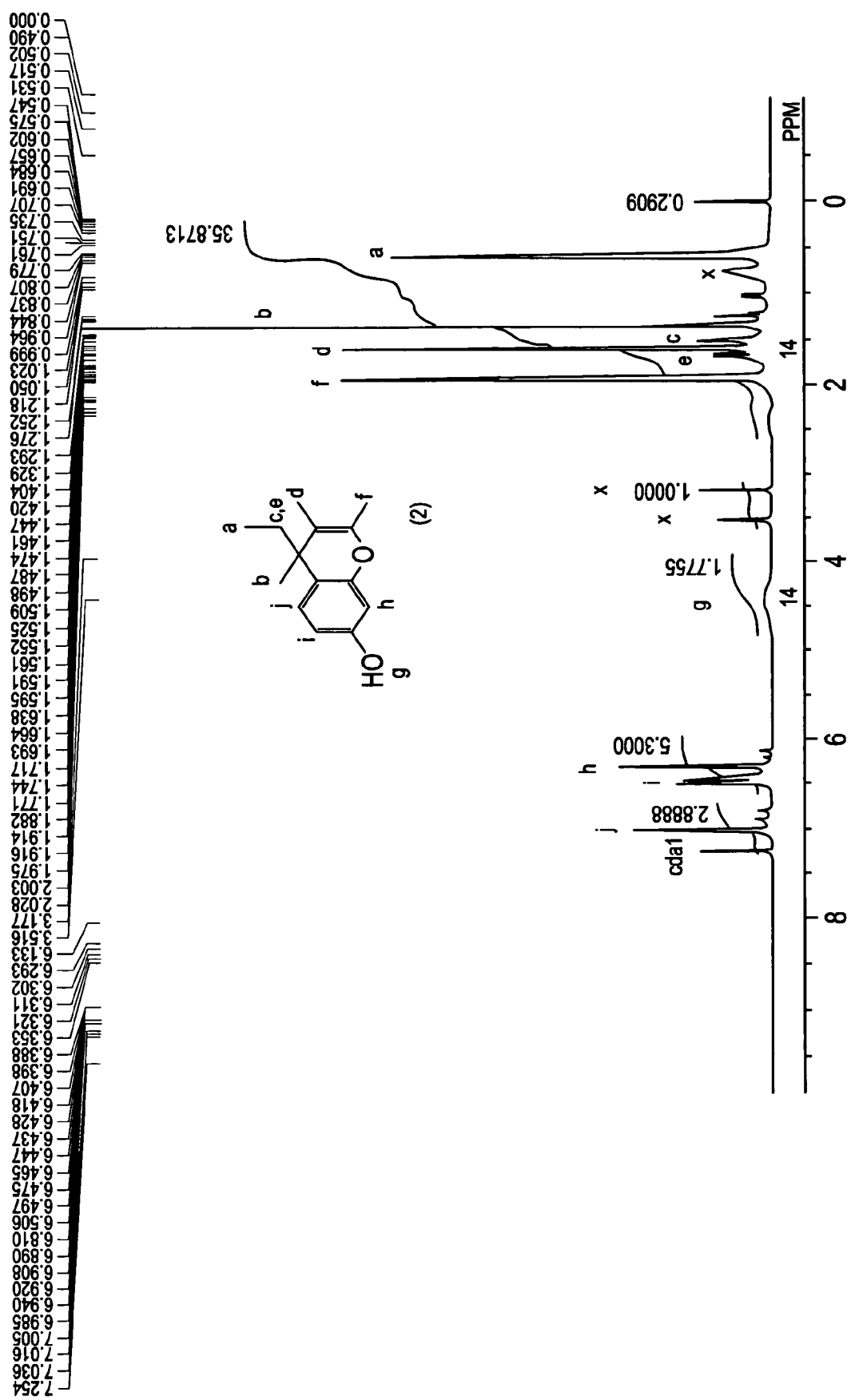
FIG. 3 is a view showing $^1$H-NMR of a compound (2) in the present invention.

A component of an elution time of 26.3 minutes in FIG. 1 was identified as a compound of the following formula (2) based on the result of its $^1$H-NMR (see FIG. 3, measuring solvent is heavy chloroform).

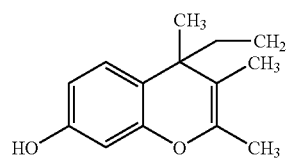
(2)

Figure 4:
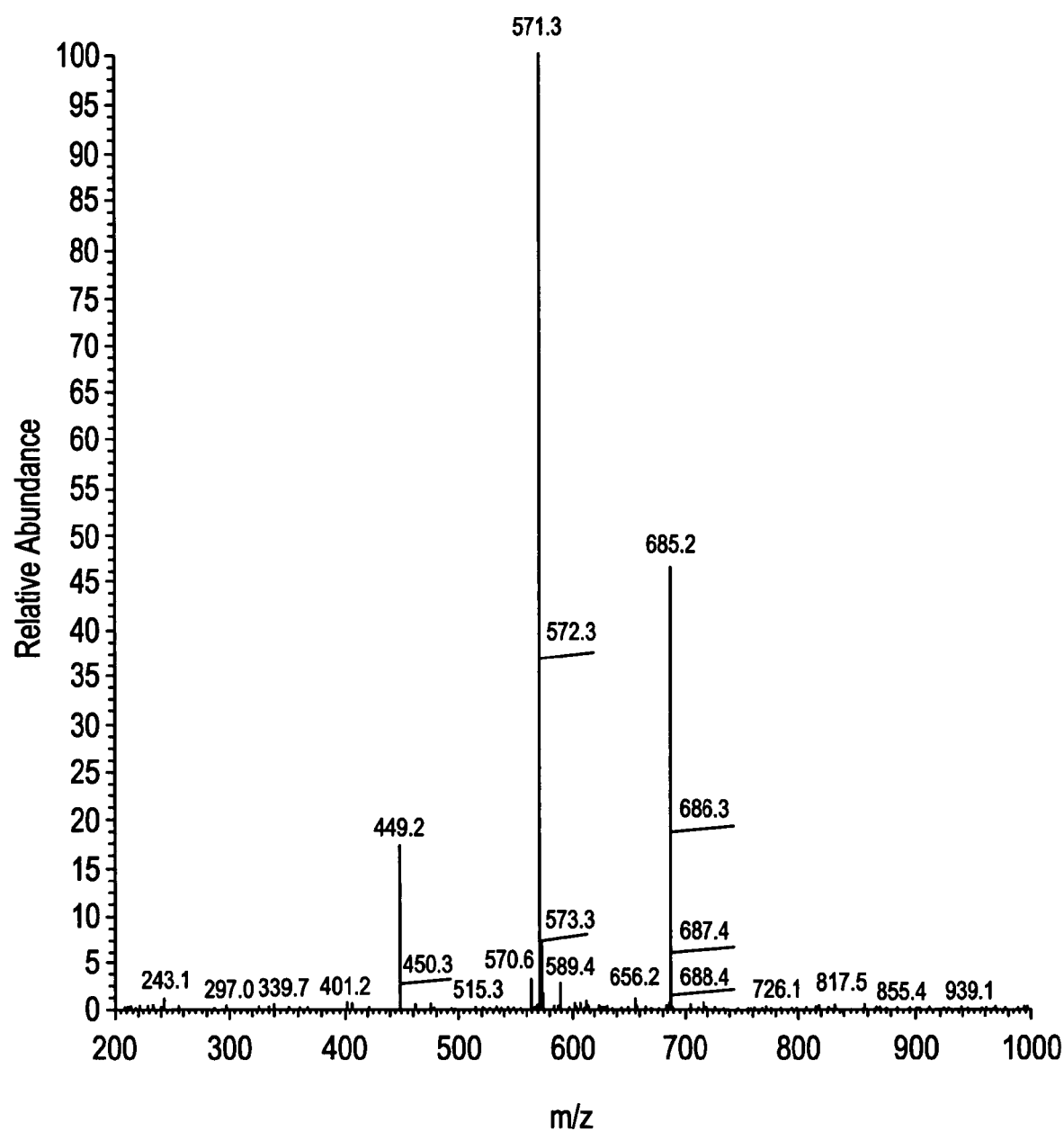
FIG. 4 is a view showing a chart of mass spectrometry of compounds (3) and (4) in the present invention.

Components of elution times of 19.9 minutes and 20.2 minutes in FIG. 1 had molecular weights of 450 and 572 (see, FIG. 4) based on the results of LC-MS, and no-discrepancy thereof with the molecular weights of the following compounds (3) and (4) was confirmed.

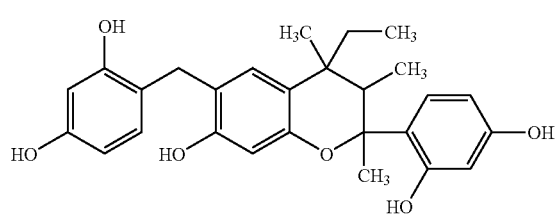
(3)

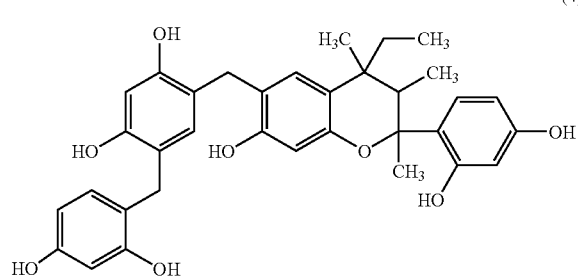
(4)

Figure 5:
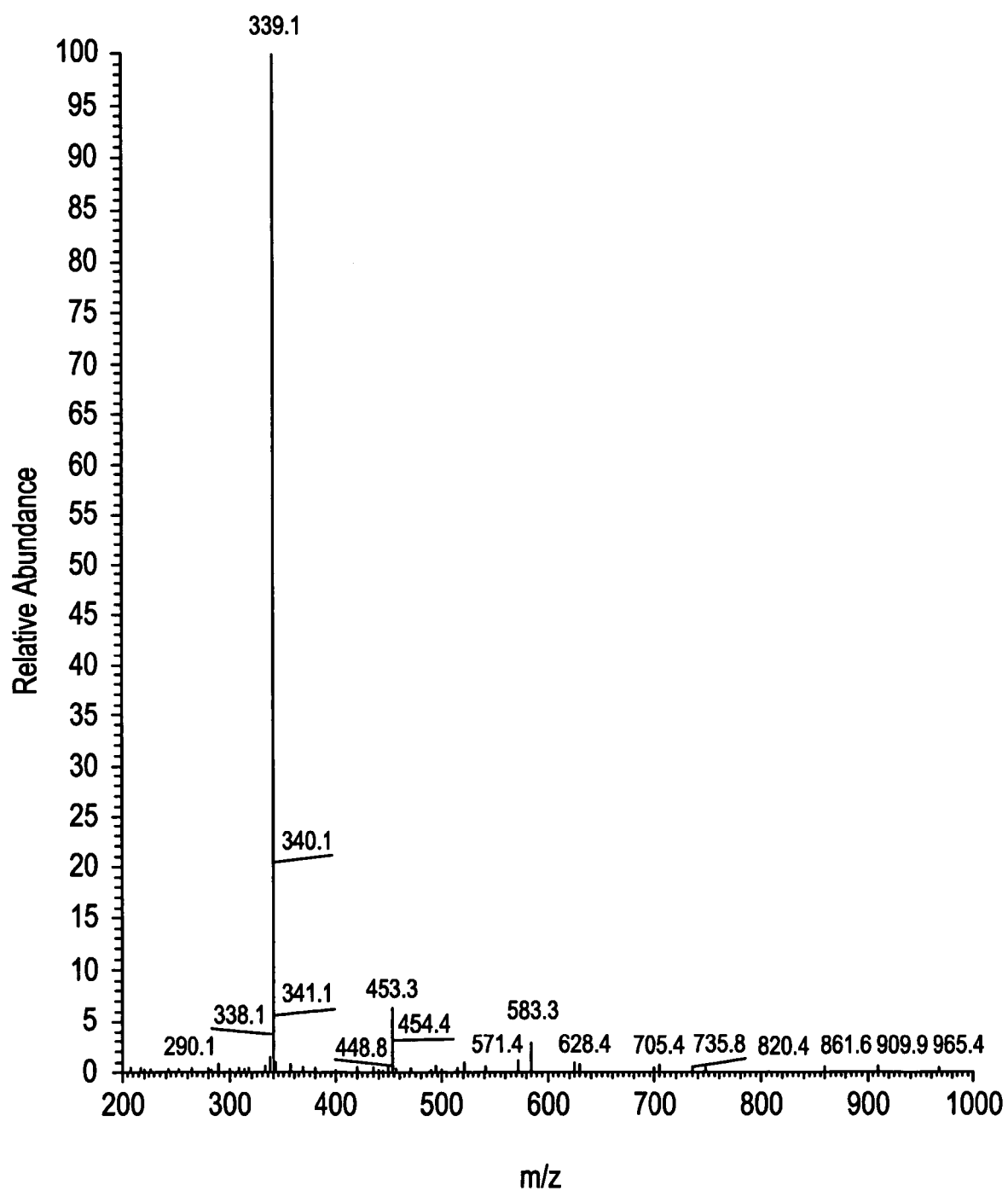
FIG. 5 is a view showing a chart of mass spectrometry of a compound (5) in the present invention.
Figure 6:
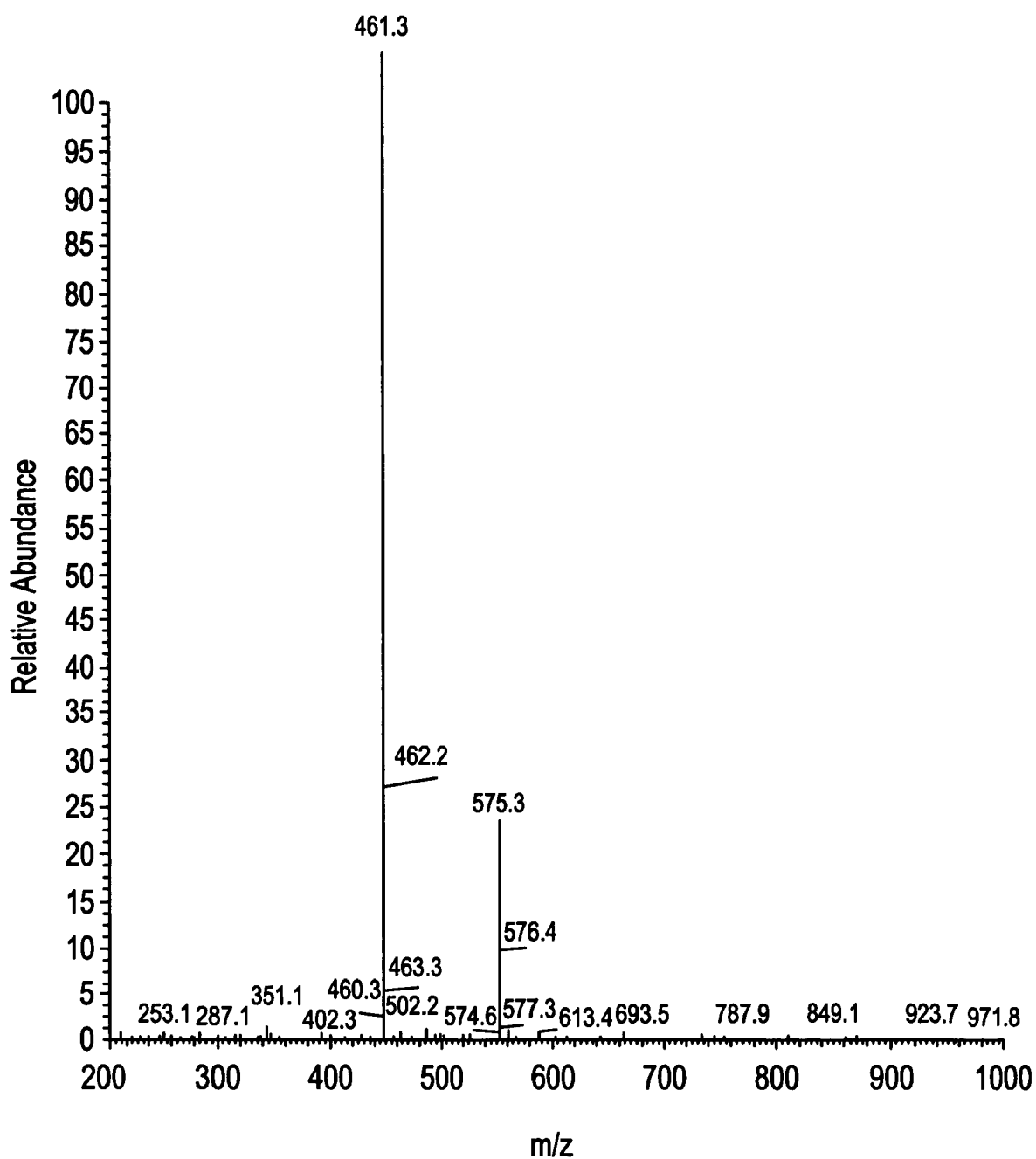
FIG. 6 is a view showing a chart of mass spectrometry of a compound (6) in the present invention.

Further, components of elution times of 23.45 minutes and 24.65 minutes in FIG. 1 had molecular weights of 340 and 462 (see, FIGS. 5, 6) based on the measurement results of LC-MS, and no-discrepancy with the following compounds (5) and (6) was confirmed.

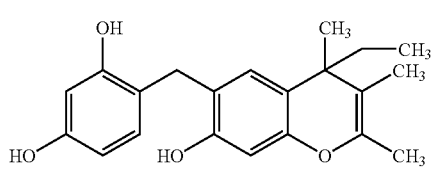
(5)

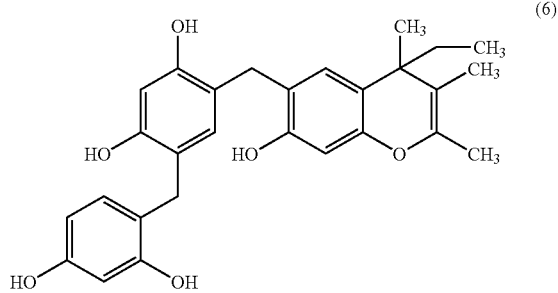
(6)

Comparative Example 1

A resorcin/formaldehyde resin was obtained in the same manner as in Example 1 except that methyl ethyl ketone was not added, the solution was kept at about 60° C. for about 100 minutes after completion of dropping formalin, and 15 g of 25% ammonia water was added. About 300 g of a resorcin/formaldehyde resin having a solid content of 50% was obtained. The resorcin content in this resin was 8.1%.

Comparative Example 2

A resorcin/formaldehyde resin was obtained in the same manner as in Example 1 except that methyl ethyl ketone and calcium chloride were not added, the solution was kept at about 60° C. for about 120 minutes after completion of dropping formalin, and 35 g of 25% ammonia water was added. About 300 g of a resorcin/formaldehyde resin having a solid content of 50% was obtained. The resorcin content in this resin was 23.1%.

Comparative Example 3

A resorcin/formaldehyde resin was obtained in the same manner as in Example 1 except that methyl ethyl ketone and calcium chloride were not added and 177.5 g of a 37% formalin aqueous solution were used. About 300 g of a solid body were obtained. The obtained solid body could not dissolve to THF, so analysis could not be performed.

INDUSTRIAL APPLICABILITY

A resorcin/formaldehyde/methyl ethyl ketone-based resin composition of the present invention is useful as an adhesive for adhering wood with other organic materials and the like.

Further, a compound (I) and compound (II) of the present invention and specific examples thereof, compounds (1) to (6), and a composition containing the compounds (1) to (6) are respectively useful as an adhesive force reinforcing component in a resorcin/formaldehyde/methyl ethyl ketone-based resin.

What is claimed is:

1. A compound of the following formula:

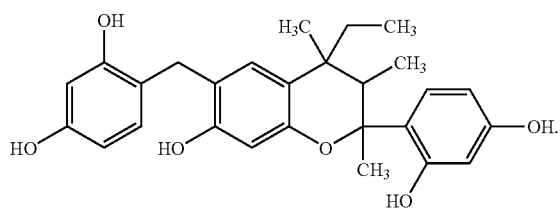

2. A compound of the following formula:

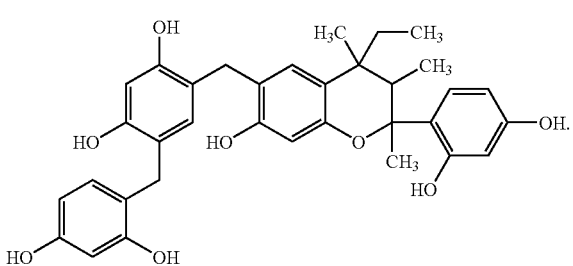

3. A compound of the following formula:

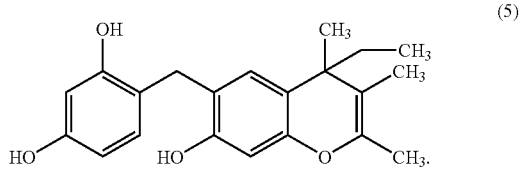

(5)

4. A compound of the following formula:

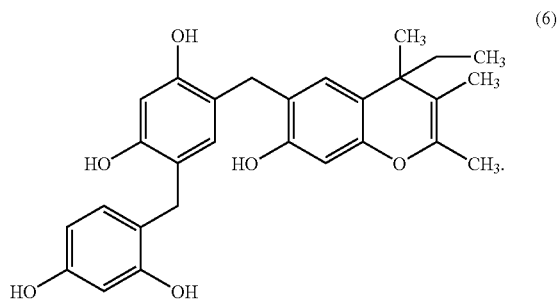

(6)

5. An adhesive composition comprising at least one compound selected from the group consisting of

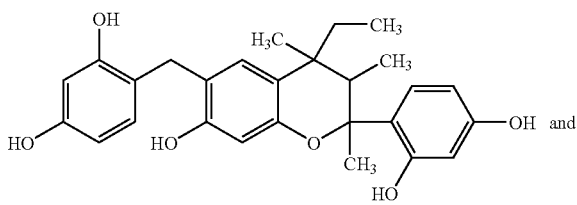

and

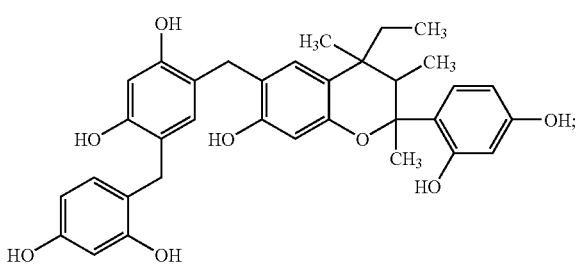

and at least one compound selected from the group consisting of

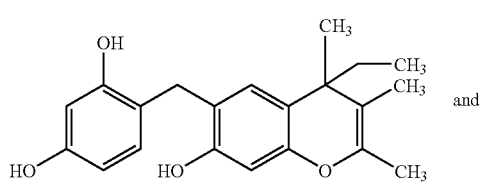

and

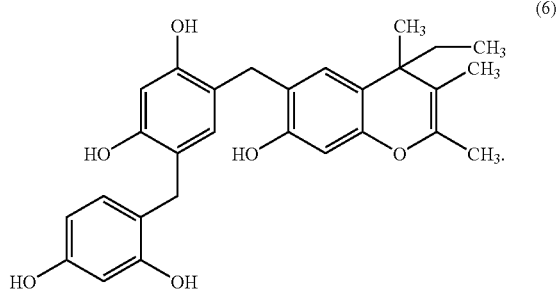

(6)

6. The adhesive composition according to claim 5, wherein the composition is obtained by reacting resorcin, formaldehyde and methyl ethyl ketone in the presence of water, salts and acidic catalyst.

7. The adhesive composition according to claim 6, wherein the salts are calcium chloride, sodium sulfate or a mixture of calcium chloride and sodium sulfate.

8. The adhesive composition according to claim 6, wherein the salts are used in an amount of 0.1 to 10 mol per mol of resorcin.

* * * * *